US007122000B1

(12) United States Patent
Poer

(10) Patent No.: US 7,122,000 B1
(45) Date of Patent: Oct. 17, 2006

(54) METHOD OF USING A WATER PIPE

(76) Inventor: Anthony Poer, 8830 Shamu Ct., Las Vegas, NV (US) 89147

( * ) Notice: Subject to any disclaimer, the term of this patent is extended or adjusted under 35 U.S.C. 154(b) by 307 days.

(21) Appl. No.: 10/631,417

(22) Filed: Jul. 30, 2003

(51) Int. Cl.
*A61F 5/00* (2006.01)
*A24F 1/14* (2006.01)

(52) U.S. Cl. ........................................ 600/38; 131/173

(58) Field of Classification Search ............ 600/38–41; D27/162; 131/200, 191, 179, 173
See application file for complete search history.

(56) References Cited

U.S. PATENT DOCUMENTS 722,405 A 3/1903 Ganim
3,375,381 A 3/1968 Tavel
3,863,646 A 2/1975 Kahler
3,872,872 A 3/1975 Kahler
3,918,464 A * 11/1975 Kolodziej ................... 131/173
4,031,904 A 6/1977 Karl
D246,389 S * 11/1977 Graham ..................... D27/162
4,148,327 A * 4/1979 Graham ...................... 131/173
4,171,703 A 10/1979 Locke
4,183,365 A 1/1980 Kelley
4,187,885 A * 2/1980 Kahler ........................ 138/89
4,201,230 A 5/1980 Howell, Jr.
D256,506 S * 8/1980 Graham ..................... D27/162
4,216,785 A 8/1980 Erickson et al.
4,241,741 A 12/1980 Cabados et al.
4,253,475 A 3/1981 Schreiber et al.
D381,116 S * 7/1997 Richards .................... D27/162
D403,106 S * 12/1998 Barmes ..................... D27/162
RE36,105 E * 2/1999 Newman ................... D27/162

* cited by examiner

*Primary Examiner*—Samuel G Gilbert
(74) *Attorney, Agent, or Firm*—Robert Ryan Morishita; Anderson & Morishita, LLC

(57) ABSTRACT

A water pipe providing sexual stimulation includes a tube with an exit port at its upper end, an reservoir port at its lower end, and an inlet port. The inlet port is spaced from the lower end whereby the inlet port remains exposed when the lower end is inserted into a vagina. The lower end cooperates with the wall of the vagina to form a water reservoir holding water in the lower end and the vagina. A stem is received into the inlet port with an end opening submerged in the water reservoir. Suction applied at the exit port draws air through the stem to bubble through the water reservoir to generate stimulatory vibrations transmitted to the vagina. Optionally, a bowl holding combustible material communicates with the stem such that smoke bubbles through the water reservoir to simultaneously filter and cool the smoke and generate stimulatory vibrations.

19 Claims, 5 Drawing Sheets

METHOD OF USING A WATER PIPE

FIELD OF THE INVENTION

The present invention relates to water pipes, also referred to as bongs, and sexual stimulation devices. More specifically, the present invention is a water pipe shaped to be inserted into, and thereby utilize, the vagina as a water reservoir to provide sexual stimulation during use of the water pipe, which may optionally be used to smoke.

BACKGROUND OF THE INVENTION

Water pipes have a long history beginning in the near east in such regions as Persia. Water pipes come in a variety of forms from hookahs and narghiles to bongs. An example of a hookah is shown in U.S. Pat. No. 722,405 and an example of a bong is shown in U.S. Pat. No. 4,216,785. As shown, the distinction between the hookah and the bong is that the hookah includes a long flexible tube, or in some instances, a number of long flexible tubes, through which the smoke travels from the pipe to the smoker's lungs, whereas the bong includes no such tube and the smoke is drawn directly from the pipe.

The operating principle of these water pipes is similar. A pipe with one open end and one closed end contains water. The material to be smoked is packed into a bowl which terminates in a stem below the water level. As air is inhaled from the open end, the air pressure in the pipe is reduced. Air and smoke travel from the bowl through the stem, through the water, into the headspace in the pipe above the water level, and into the smoker's lungs. Some smokers believe that as the smoke is drawn through the water, the smoke is cooled and particulate matter is filtered out making the smoke easier on the lungs.

There is some minor variation in the water pipe art, however, all prior art devices include a closed chamber for a water reservoir to prevent the water from communicating outside the water pipe. While some water pipes, such as that shown in U.S. Pat. No. 4,031,904, include removable bases to facilitate cleaning, all water pipes, including those with removable bases are intended to be used with the bases securely closing the chamber to contain the water.

Devices for sexual stimulation have a similarly long history. Any number of vibrators and other artificial sexual aids are known in the art. Simpler devices merely use shape and material to provide stimulation. However, more complex devices are generally characterized by the use of electrical means and/or mechanical means to create motion or vibration that stimulates the user. One example is U.S. Pat. No. 3,375,381 which shows an electric motor spinning an eccentrically mounted weight to create a regular vibration. However, no prior art device was found to use a fluid or fluid motion to create stimulatory vibrations.

SUMMARY OF THE INVENTION

A water pipe for providing female sexual stimulation includes an elongate tube. The tube has an open exit port at its upper end, an open reservoir port at its lower end, and an open inlet port. In one optional embodiment, the exit port forms a mouthpiece. In an alternate optional embodiment, a plug with a hole is disposed in the exit port, with the hole communicating with the exit port. In such an optional embodiment, a flexible hose includes a first end communicating with the hole in the plug and a second end serving as a mouthpiece. In yet another embodiment, a flexible tube communicates directly with the exit port.

The inlet port is spaced from the lower end to permit the lower end to be inserted into a vagina. Optionally, when the lower end is inserted, the inlet port remains exposed to ambient air. In one optional embodiment, the inlet port is disposed at an intermediate point along the water pipe between the upper end and the lower end. In an alternate optional embodiment, the inlet port is disposed proximate the upper end. In an optional embodiment described above including a plug disposed in the upper end, the inlet port may be disposed in the plug. In any optional embodiment, the lower end cooperates with the wall of the vagina to form a water reservoir holding water in the lower end and the vagina with the reservoir port submerged such that water rests in the vagina and at least a portion of the lower end.

In an optional embodiment, the pipe includes a flare separating the lower end, and the reservoir port located thereat, from the inlet port. In a further optional embodiment, the flare is an integral bulb.

A stem with an end opening is received into the inlet port with a substantially airtight seal with the end opening submerged in the water reservoir formed by the lower end in cooperation with the wall of the vagina. The other end of the stem is exposed to ambient air. When suction is applied at the exit port, air is drawn through the stem to bubble through the water reservoir thereby generating stimulatory vibrations that are transmitted to the vagina.

In a further optional embodiment, a bowl for holding combustible material communicates with the stem such that the bowl is exposed to ambient air. In such an optional embodiment, the combustible material is ignited such that when suction is applied at the exit port, smoke from the combustible material is drawn through the stem to bubble through the water reservoir thereby filtering and cooling the smoke in addition to generating stimulatory vibrations that are transmitted to the vagina. Optionally, the smoke may collect in a smoke collection chamber between the upper end and the lower end.

DESCRIPTION

Figure 1:
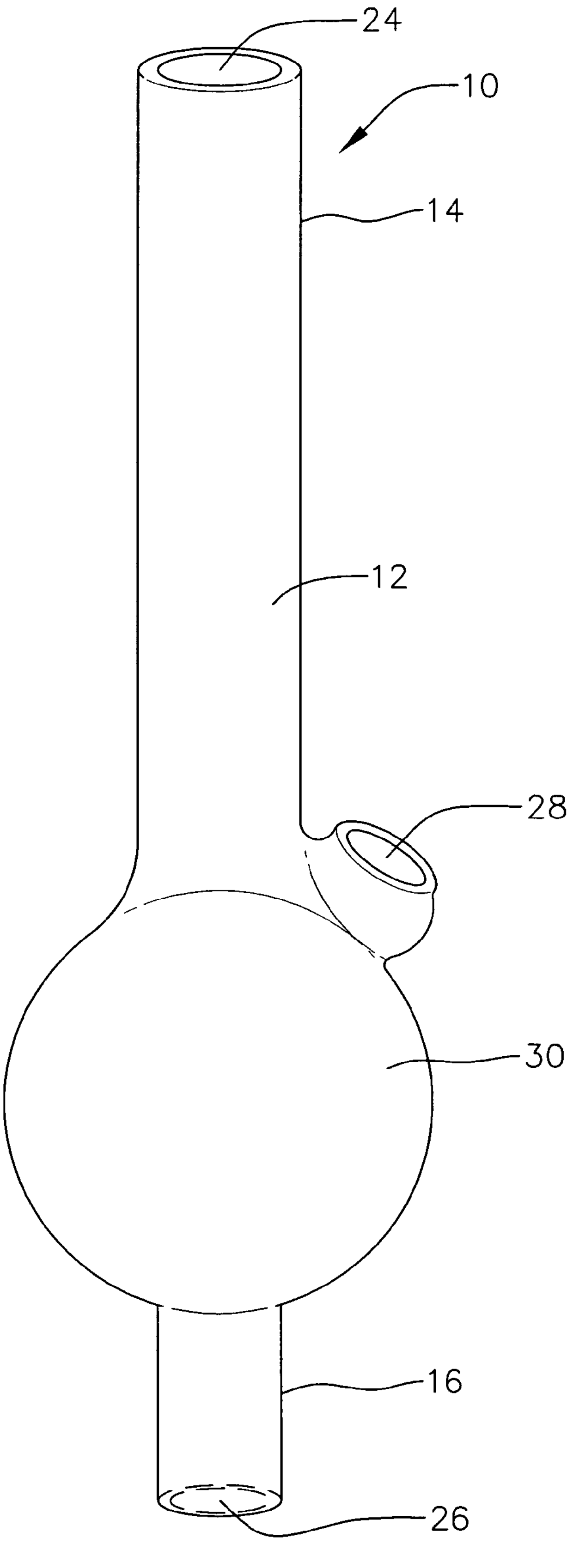
FIG. 1 is an elevated perspective view of a device according to an embodiment of the present invention.
Figure 2:
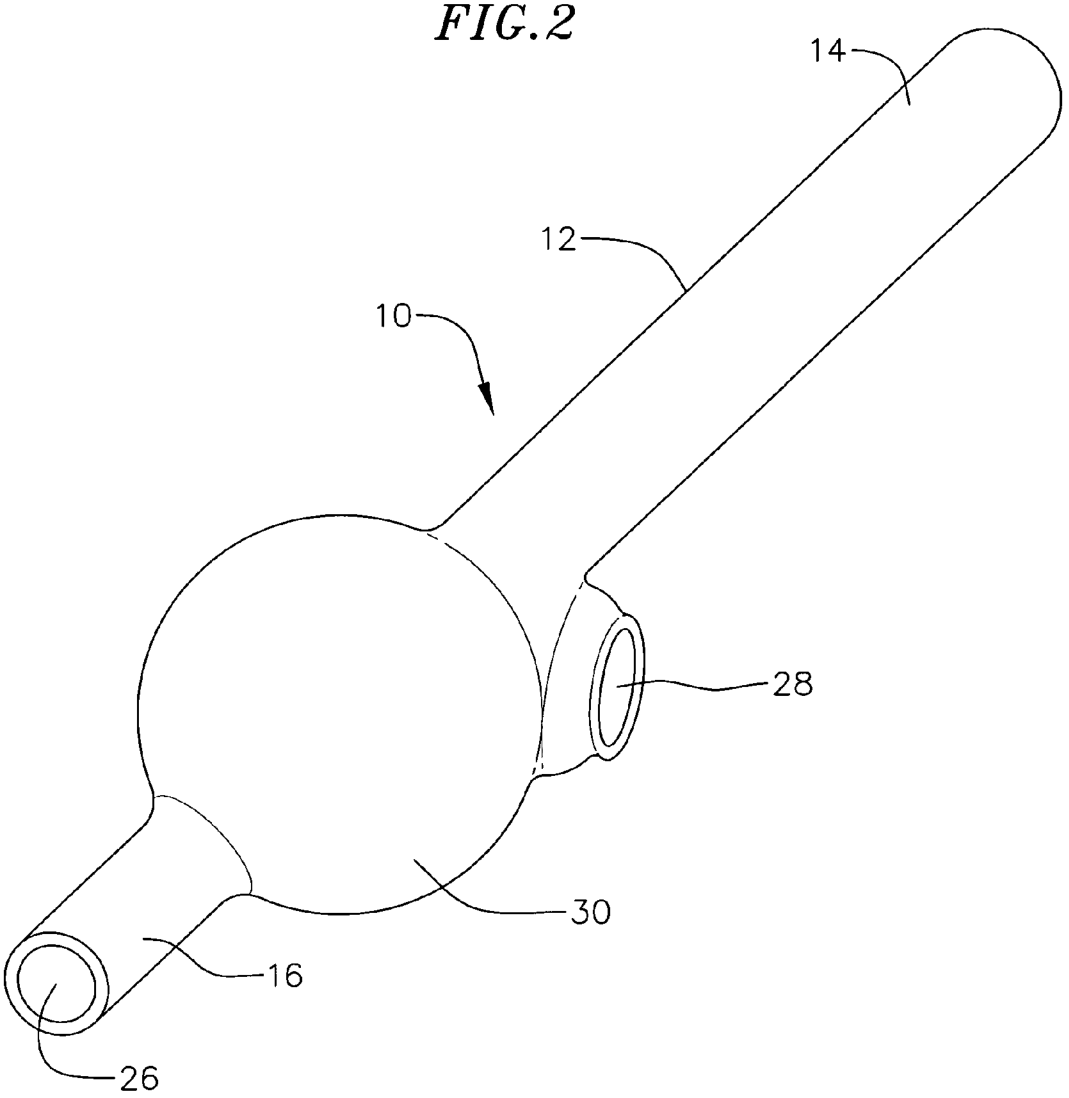
FIG. 2 is a bottom perspective view of a device according to the embodiment of FIG. 1.

Reference is now made to the figures wherein like parts are referred to by like numerals throughout. It should be noted that the figures show a number of different embodiments for the present invention, including embodiments adapted for smoking as well as an embodiment primarily for sexual stimulation not necessarily adapted for smoking. Each of these embodiments is described in turn. With reference to FIG. 1, the present invention is a water pipe 10. The water pipe 10 is formed from an elongate tube 12 with an upper end 14 and a lower end 16. In an optional embodiment adapted for smoking, such as that shown in FIGS. 3–5, a smoke collection chamber 18 may be disposed between the upper end 14 and the lower end 16. While the tube 12 may be formed of any material, it should be noted that the embodiments adapted for smoking use could be formed from glass, acrylic, ceramic, polymers, or other heat-tolerant material.

Returning to FIG. 1, each of the upper end 14 and lower end 16 includes a port. Specifically, the upper end 14 includes an exit port 24 and the lower end 16 includes an open reservoir port 26.

Turning first to the upper end 14, the exit port 24 and upper end 14 may be shaped in any manner. For example, in the optional embodiment shown in FIG. 3, the exit port 24 is an opening across the face of the upper end 14 and the upper end 14 forms a mouthpiece. As shown in the optional embodiment of FIGS. 4 and 5, the exit port 24 may receive a plug 20 that enables the exit port 24 to communicate with a flexible tube 22. In either case, the exit port 24 serves as an airway to transmit pressure changes in the water pipe 10 and, in an optional embodiment, carry smoke.

Referring again to FIG. 1, because the lower end 16 is used for sexual stimulation, it is contemplated that the lower end 16 could be shaped into a variety of forms. That is, the lower end 16 need not necessarily be cylindrical as shown in the figures but may take any shape, including, for example, tapered, flared, phallic, or the like. Additionally, it is contemplated that the lower end 16 may optionally be covered with fixed or removable coverings so long as the reservoir port 26, described in greater detail below, is not obstructed.

The reservoir port 26 at the lower end 16 may similarly take a variety of forms. However, unlike the exit port 24, the reservoir port 26 aids in the formation of a water reservoir. That is, in use, as described in greater detail below, the lower end 16 cooperates with a female vagina to form a water reservoir. The reservoir port 26 is submerged in the water reservoir and allows water and bubbles, and the vibrations created by the bubbles in the water, to be transmitted to the vaginal walls. As shown in FIGS. 1–5, the reservoir port 26 may optionally take the form of an opening across the face of the lower end 16. However, it is contemplated that the reservoir port 26 may be of any size or shape and may be located anywhere along the lower end 16.

The tube 12 also includes an inlet port 28. The inlet port 28 is spaced from the lower end 16 to permit the lower end 16 to be inserted into a vagina. Optionally, the inlet port 28 is positioned such that when the lower end 16 is inserted into a vagina, the inlet port 28 remains exposed to ambient air to permit air to be drawn into the tube 12 through the inlet port 28. In an optional embodiment, a flare 30 separates the inlet port 28 from the lower end 16. This flare 30 may take any shape including the integral bulb shown in FIGS. 1–5.

The water pipe 10 is used in conjunction with a hollow stem 32 with an end opening 34. It is noted that the stem 32 could be integrally formed with the tube 12. However, in the optional embodiment of FIGS. 3–5, the stem 32 is separate from the tube 12 and is received into the inlet port 28.

Figure 3:
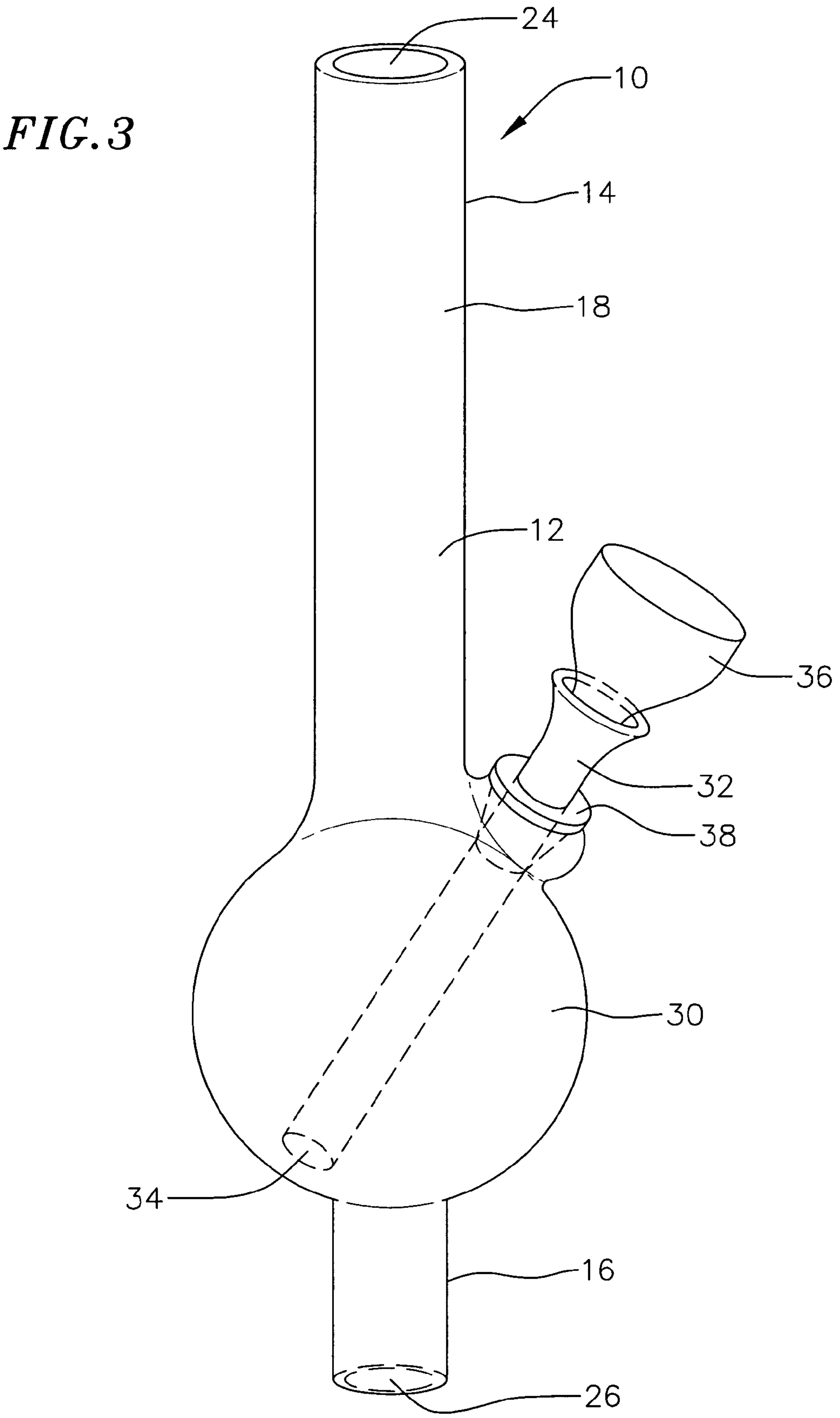
FIG. 3 is an elevated perspective view of a device according to an alternate embodiment of the present invention.
Figure 4:
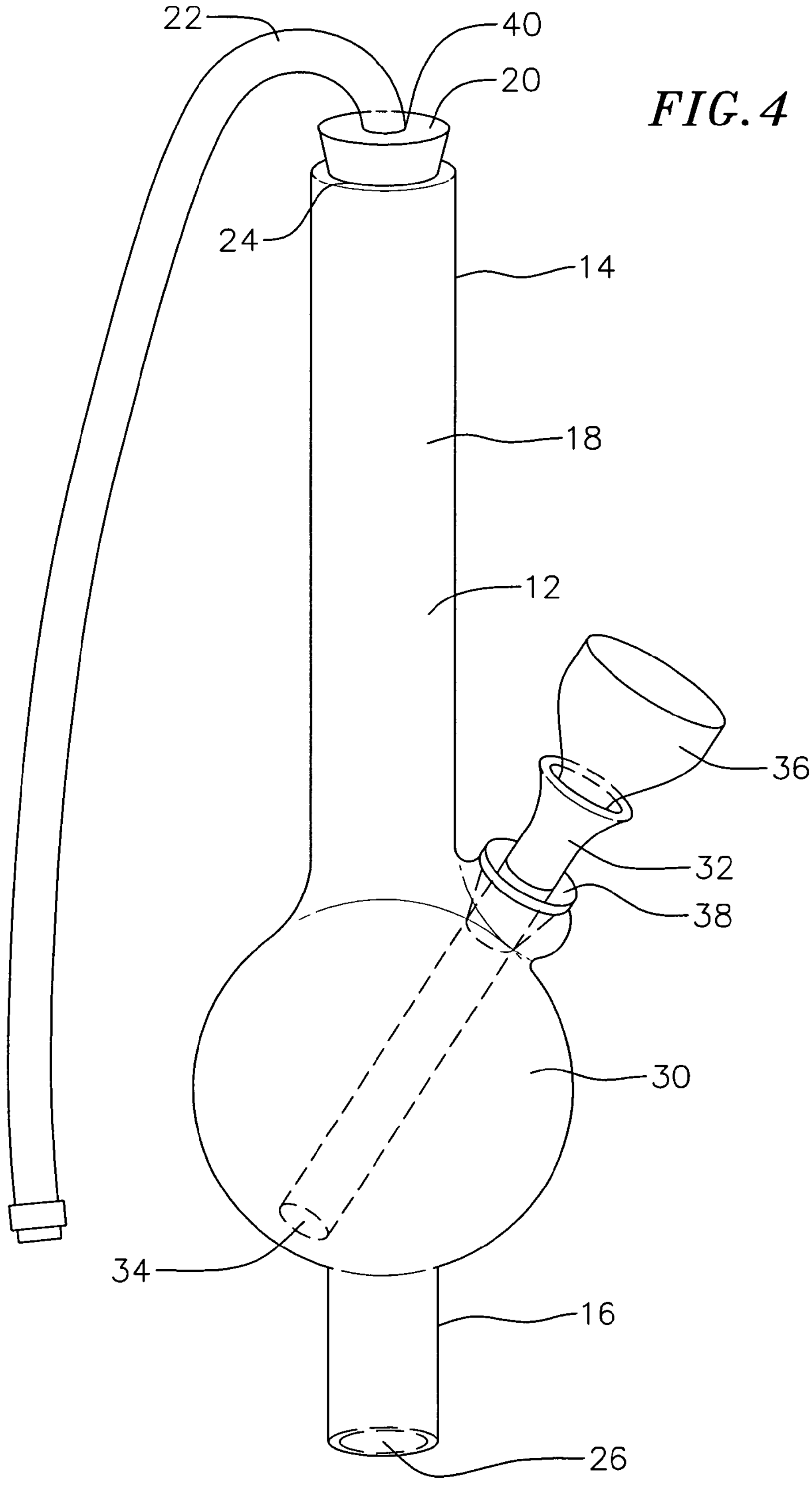
FIG. 4 is an elevated perspective view of a device according to an alternate embodiment of the present invention.
Figure 5:
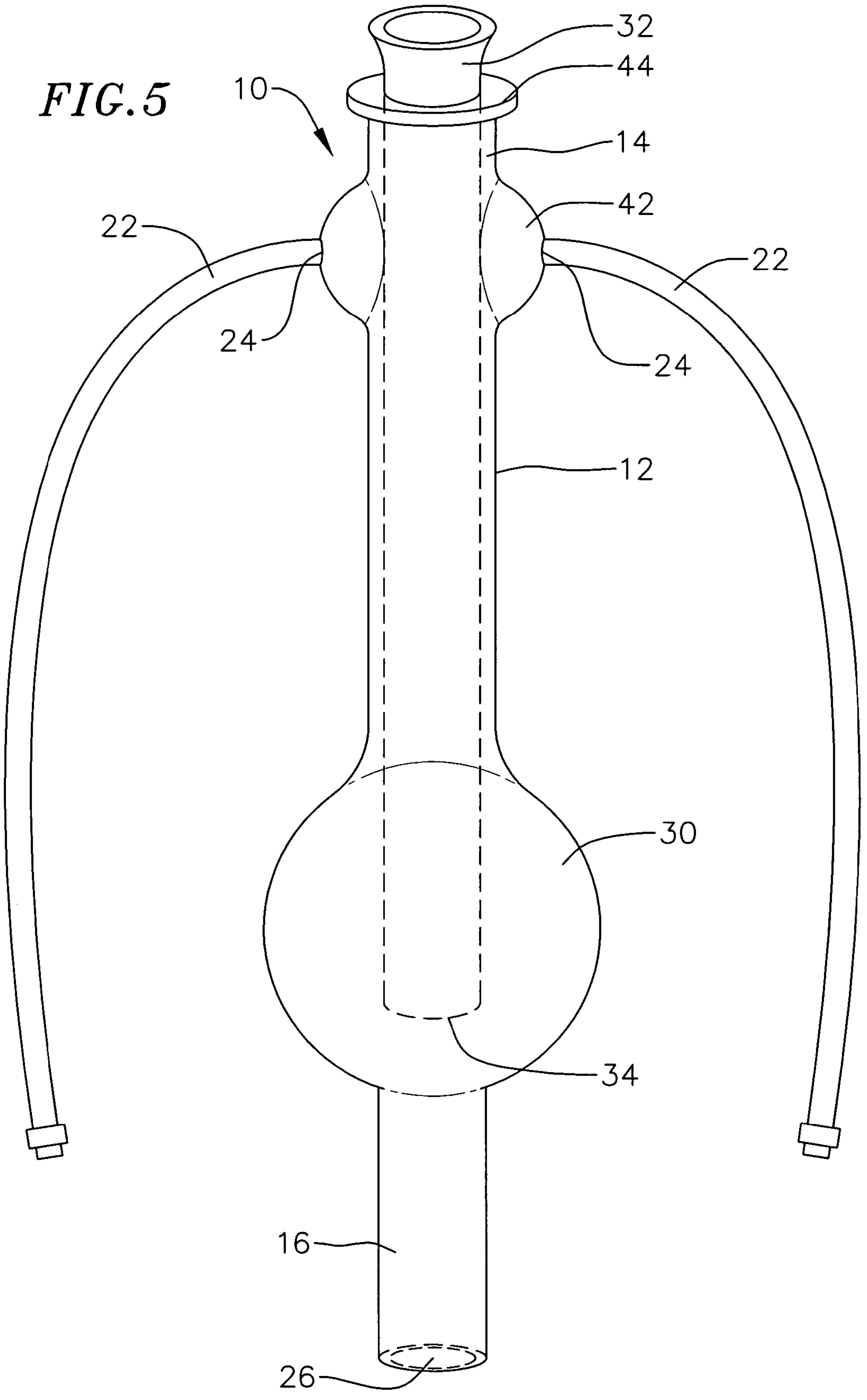
FIG. 5 is an elevated perspective view of a device according to an alternate embodiment of the present invention.

In optional embodiments adapted for smoking, such as those shown in FIGS. 3–5, the inlet port 28 receives a stem 32 in communication with a bowl 36. The stem 32 and bowl 36 may be separate mating parts, as shown in FIGS. 3–5, or may be integrally formed. While the bowl 36 and stem 32 may be formed from any material, it is noted that in an embodiment adapted for smoking, the bowl 36 holds the combustible material and, thus, the bowl 36 and stem 32 should be formed from a heat-resistant material. Optionally, an airtight seal is formed between the inlet port 28 and the stem 32 using an optional grommet 38.

In an alternate embodiment used primarily for sexual stimulation and not necessarily for smoking, such as that shown in FIG. 1, the bowl 36 need not be included. In a further optional embodiment, the bowl 36 may be replaced with an air regulator that regulates the air intake and carries air to below the water level in the water reservoir as described in greater detail below. For example, a stopper with a hole therethrough may be applied to the stem 32 to regulate the flow of air through the stem 32 to create the pressures desired to carry air into the water reservoir and create bubbles in a manner described in greater detail below.

As alluded to above, in an optional embodiment, shown in FIGS. 4 and 5, one or more flexible tubes 22 may be connected to the upper end in communication with the exit port. The flexible tube 22 is optionally a flexible polymer such as rubber tube, silicon tube, surgical tubing, or the like. It is noted that the flexible tube 22 in such embodiments may facilitate self-stimulation. That is, the flexible tube 22 may be of a length to permit a female to provide the applied suction used to generate the stimulatory vibrations in the water reservoir while the lower end 16 is inserted into her vagina.

For example, in the embodiment of FIG. 4, a plug 20 with a hole 40 therethrough has been inserted into the upper end 14 with the hole 40 in communication with the exit port 24. Additionally, a flexible tube 22 is attached to the plug 20 with one end in communication with the exit port 24. This enables the other end of the flexible tube 22 to be used as a mouthpiece to apply suction in a manner described in greater detail below.

Similarly, in FIG. 5, multiple flexible tubes 22 may communicate with one or more exit ports 24 located around the surface of the tube 12 on an optional expansion 42. It is also noted that in such an optional embodiment, the inlet port 28 may be located at a plug 44 disposed in the upper end 14 with a stem 32 extending down the tube 12 to below the water level.

In use, the lower end 16 is inserted into the vagina such that the lower end 16 cooperates with the vagina to form a water reservoir. The water reservoir is filled, such as by pouring water down the tube 12 through the exit port 24, through the tube 12, through the reservoir port 26, and into the vagina to fill the vagina and a portion of the lower end 16 with water such that the reservoir port is submerged. Thus, water, bubbles, and the vibrations created by such bubbles, pass freely through the reservoir port 26 to the vagina.

The stem 32 is inserted into the inlet port 28 and positioned with the end opening 34 submerged below the water level of the water reservoir and the other end exposed to ambient air. As discussed above, an optional bowl 36 or air regulator may be attached to the stem 32 in communication therewith. In an embodiment including a plug 20 in the upper end, the plug 20 is positioned with the hole 40 in communication with the exit port 24.

Suction is applied at the exit port 24. As discussed above, this will typically be done through a mouthpiece either formed by the upper end 14 or at the end of a flexible tube 22. Air is drawn through the stem 32 to bubble through the water reservoir. The bubbles travel through the water reservoir and burst at the water level. This bubbling creates stimulatory vibrations in the water reservoir that are transmitted to the vagina.

In an embodiment used for smoking, the combustible material to be smoked is packed into the bowl 36 and ignited. When suction is applied at the exit port 24, smoke travels through the stem 32 and bubbles through the water reservoir. As above, the bubbling creates stimulatory vibrations in the water reservoir that are transmitted to the vagina. Simultaneously, the smoke bubbling though the water reservoir is cooled and filtered. The smoke bubbles burst at the water level and travel through the smoke collection chamber 18 to the exit port 24. In the optional embodiment in which the upper end 14 forms a mouthpiece, the smoke may be inhaled at the upper end 14. In the optional embodiment in which a flexible tube 22 is used, the smoke travels through the exit port 24, through the flexible tube 22, and to a mouthpiece where it is inhaled.

While certain embodiments of the present invention have been shown and described it is to be understood that the present invention is subject to many modifications and changes without departing from the spirit and scope of the claims presented herein.

I claim:

1. A method of using a water pipe for providing female sexual stimulation, comprising:

providing an elongate tube, the tube having an open exit port at its upper end, an open reservoir port at its lower end, and an open inlet port spaced from said lower end;

providing a stem with an end opening;

inserting said lower end into a vagina such that said lower end cooperates with the wall of said vagina to form and maintain a water reservoir;

filling the water reservoir to hold water in said lower end and said vagina with said reservoir port open and submerged;

receiving said stem into said inlet port with a substantially airtight seal with said end opening submerged in said water reservoir and the other end exposed to ambient air; and applying suction at said exit port to draw air through said stem to bubble through said water reservoir thereby generating stimulatory vibrations that are transmitted through said open reservoir port to said vagina.

2. The method of claim 1 further comprising:

providing a bowl communicating with said stem for holding combustible material; and igniting said combustible material such that applied suction at said exit port causes smoke from said combustible material to bubble through said water reservoir thereby filtering and cooling said smoke.

3. The method of claim 1 wherein said elongate pipe further includes a flare separating said lower end from said inlet port.

4. The method of claim 3 wherein said flare is an integral bulb.

5. The method of claim 1 wherein said upper end of said water pipe forms a mouthpiece.

6. The method of claim 1 further comprising:

providing a plug with a hole therethrough, said plug disposed in said upper end with said hole communicating with said exit port; and providing a flexible tube having two ends, a first end communicating with said hole and a second end forming a mouthpiece such that suction applied at the second end is communicated to said exit port via said flexible tube.

7. The method of claim 1 further comprising providing a plug disposed in said upper end wherein said inlet port is disposed in said plug; and providing a flexible tube having two ends, a first end communicating with said exit port and a second end forming a mouthpiece such that suction applied at the second end is communicated to said exit port via said flexible tube.

8. A method of using a water pipe for providing female sexual stimulation while smoking combustible material, said combustible material held in a bowl communicating with a hollow elongate stem with an end opening, comprising:

providing an elongate tube, the tube having an open exit port at its upper end, an open reservoir port at its lower end permitting the free passage of water therethrough, a smoke collection chamber between said upper end and said lower end, and an open inlet port receiving said stem, said inlet port spaced from said lower end;

inserting said lower end into a vagina, said lower end cooperating with the wall of said vagina to form and maintain a water reservoir with said reservoir port open and submerged;

filling said water reservoir with water;

receiving said stem into said inlet port with a substantially airtight seal with said end opening submerged in said water reservoir and said bowl exposed to ambient air;

igniting said combustible material; and applying suction at said exit port to cause smoke from said combustible material to bubble through said water reservoir thereby filtering and cooling said smoke and simultaneously generating stimulatory vibrations that are transmitted through said open reservoir port to said vagina, said smoke then drawn through said smoke collection chamber to said exit port.

9. The method of claim 8 wherein said elongate pipe further includes a flare separating said lower end from said inlet port.

10. The method of claim 9 wherein said flare is an integral bulb.

11. The method of claim 8 wherein said upper end forms a mouthpiece.

12. The method of claim 8 further comprising:

providing a plug with a hole therethrough, said plug disposed in said upper end with said hole communicating with said exit port; and providing a flexible tube having two ends, a first end communicating with said hole and a second end forming a mouthpiece such that suction applied at the second end is communicated to said exit port via said flexible tube.

13. The water pipe of claim 8 further comprising providing a plug disposed in said upper end wherein said inlet port is disposed in said plug; and providing a flexible tube having two ends, a first end communicating with said exit port and a second end forming a mouthpiece such that suction applied at the second end is communicated to said exit port via said flexible tube.

14. A method of using water pipe for providing female sexual stimulation while smoking combustible material, said combustible material held in a bowl communicating with a hollow elongate stem with an end opening, comprising:

providing an elongate tube, the tube having an open exit port at its upper end wherein said upper end forms a mouthpiece, an open reservoir port at its lower end permitting the free passage of water therethrough, a smoke collection chamber between said upper end and said lower end, and an open inlet port at an intermediate point between said upper end and said lower end receiving said stem, said inlet port spaced from said lower end such that said lower end is adapted to be inserted into a vagina leaving said inlet port exposed;

inserting said lower end into a vagina, said lower end cooperating with the wall of said vagina to form and maintain a water reservoir;

filling said water reservoir to hold water in said lower end and said vagina with said reservoir port open and submerged such that water passes freely through said open reservoir port;

receiving said stem into said inlet port with a substantially airtight seal with said end opening submerged in said water reservoir and said bowl exposed to ambient air;

igniting said combustible material; and applying suction at said exit port to cause smoke from said combustible material to bubble through said water reservoir thereby filtering and cooling said smoke and simultaneously generating stimulatory vibrations that are transmitted through said open reservoir port to said vagina, said smoke then drawn through said smoke collection chamber to said exit port.

15. The method of claim 14 wherein said elongate pipe further includes a flare separating said lower end from said inlet port.

16. The method of claim 15 wherein said flare is an integral bulb.

17. A method of using a water pipe for providing female sexual stimulation while smoking combustible material, said combustible material held in a bowl communicating with a hollow elongate stem with an end opening, comprising:

providing an elongate tube, the tube having an open exit port at its upper end, an open reservoir port at its lower end permitting the free passage of water therethrough, and a smoke collection chamber between said upper end and said lower end;

inserting said lower end into a vagina, said lower end cooperating with the wall of said vagina to form and maintain a water reservoir;

filing said water reservoir to hold water in said lower end and said vagina with said reservoir port open and submerged such that water passes freely through said open reservoir port;

providing a plug including an inlet port;

disposing said plug in said upper end such that said inlet port is spaced from said lower end, said lower end adapted to be inserted into a vagina leaving said inlet port exposed; and providing a flexible tube having two ends, a first end in substantially airtight communication with said exit port and a second end forming a mouthpiece; and receiving said stem into said inlet port with a substantially airtight seal with said end opening submerged in said water reservoir and said bowl exposed to ambient air;

igniting said combustible material; and applying suction at said exit port to cause smoke from said combustible material to bubble through said water reservoir filtering and cooling said smoke and simultaneously generating stimulatory vibrations that are transmitted through said open reservoir port to said vagina, said smoke then drawn through said smoke collection chamber to said exit port.

18. The method of claim 17 wherein said elongate pipe further includes a flare separating said lower end from said inlet port.

19. The method of claim 18 wherein said flare is an integral bulb.

* * * * *